(12) United States Patent
Birecki et al.

(10) Patent No.: US 8,045,167 B2
(45) Date of Patent: Oct. 25, 2011

(54) DETERMINING SOLID CONCENTRATION OF AN INK

(75) Inventors: Henryk Birecki, Palo Alto, CA (US); Omer Gila, Cupertino, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 450 days.

(21) Appl. No.: 12/398,538

(22) Filed: Mar. 5, 2009

(65) Prior Publication Data

US 2010/0225919 A1    Sep. 9, 2010

(51) Int. Cl.
*G01N 21/00* (2006.01)
*B41J 2/205* (2006.01)
*H01J 1/02* (2006.01)

(52) U.S. Cl. .......... 356/442; 347/15; 347/100; 347/101; 106/31.25; 106/31.6

(58) Field of Classification Search .................. 356/445, 356/432–444; 347/15, 43, 95, 100, 101; 106/31.25, 31.6; 313/29; 324/71.3, 71.1, 324/444
See application file for complete search history.

(56) References Cited

U.S. PATENT DOCUMENTS

| 5,570,193 A | 10/1996 | Landa et al. |
| 6,918,662 B2 * | 7/2005 | Arita et al. ..................... 347/100 |
| 7,306,311 B2 * | 12/2007 | Yamanobe ....................... 347/15 |
| 7,345,810 B2 * | 3/2008 | Chopra et al. ................ 359/296 |
| 7,675,298 B2 * | 3/2010 | Forgacs ......................... 324/713 |
| 2006/0125363 A1 * | 6/2006 | Tahira et al. .................... 313/29 |
| 2007/0280712 A1 | 12/2007 | Holland |

* cited by examiner

*Primary Examiner* — Sang Nguyen

(57) ABSTRACT

The present disclosure is drawn to methods, devices, and systems for determining solid content of inks, including a device comprising a chamber configured to hold an ink sample having ionic particulates in a liquid vehicle, a first opening in the chamber for filling the chamber with the ink sample, a second distinct opening in the chamber for removal of the liquid vehicle, a deposition electrode at least partially defining the chamber, a counter electrode, a power supply connected to the deposition electrode and the counter electrode for creating an electric field inside the chamber, and a densitometer optically coupleable to the deposition electrode for measuring the optical density of ionic particulates. Additionally, the device can be operable to separate the ionic particulates from the liquid vehicle by deposition of the ionic particulates at the deposition electrode and/or the device can be operable to measure the optical density of the ionic particulates after migration to the deposition electrode.

19 Claims, 1 Drawing Sheet

DETERMINING SOLID CONCENTRATION OF AN INK

BACKGROUND

Digital printing involves technologies in which a printed image is created directly from digital data, for example using electronic layout and/or desktop publishing programs. Known methods of digital printing include full-color ink-jet printing, electrophotographic printing, laser photo printing, and thermal transfer printing.

These methods rely on inks in creating text and images associated with the digital data. Many techniques have been used to improve the quality of the printing including modifying the ink with polymers, biocides, solvents, additives, stabilizers, dispersants, etc. Additionally, many types of print media have been developed to further improve the overall print quality. As such, improvement of such printing systems through ongoing research and developmental efforts continue to be sought.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
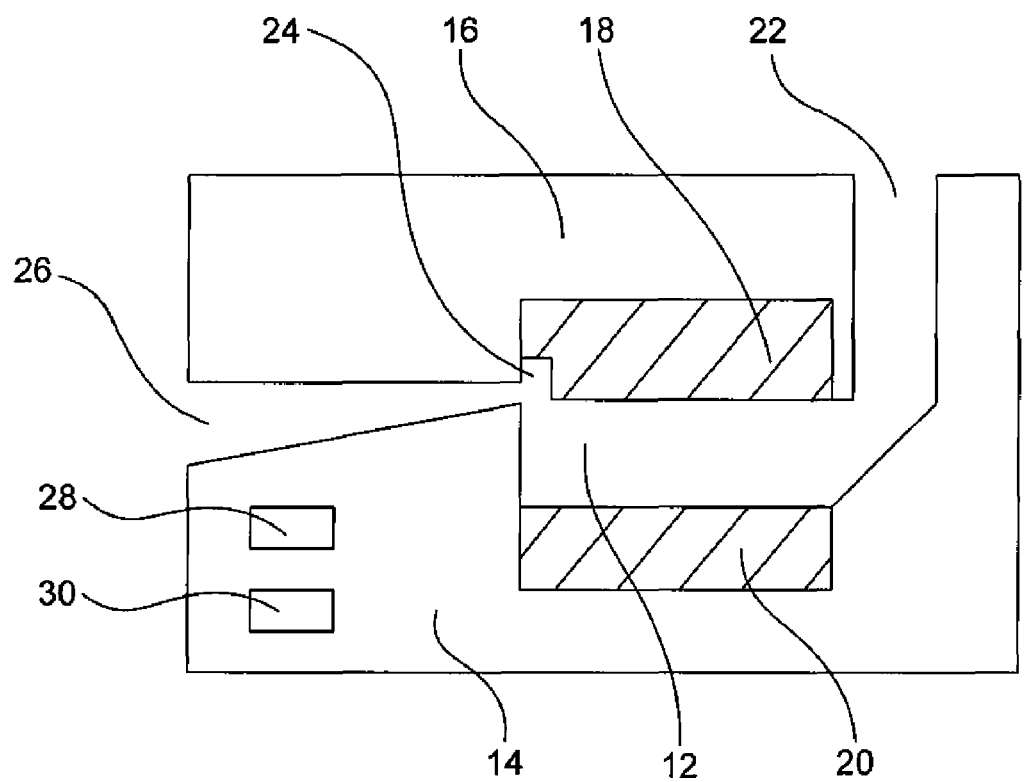
FIG. 1 is a cross-sectional view of a device for separating ionic particulates from a liquid vehicle of an ink in accordance with an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this disclosure is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the context clearly dictates otherwise.

As used herein, "liquid vehicle," "vehicle," or "liquid medium" refers to the fluid in which the colorant of the present disclosure can be dispersed to form an ink. Such liquid vehicles and vehicle components are known in the art. Typical liquid vehicles can include but are not limited to a mixture of a variety of different agents, such as surfactants, co-solvents, buffers, biocides, sequestering agents, compatibility agents, antifoaming agents, oils, emulsifiers, viscosity modifiers, etc.

As used herein, "liquid electrophotographic ink" or "LEP ink" generally refers to an ink including a liquid vehicle, a colorant, and a charging component.

As used herein, "ionic particulate" refers to any charged solid present, suspended, or dispersed in an ink as described herein. Generally, an "ionic particulate" has a positive or negative charge, although the particulate may also have both types of charges. For example, a solid having both a positive and negative charge qualifies as an ionic particulate even though the particulate may be neutral; i.e., the net charge on the particulate may be zero.

As used herein, "colorant" can include dyes and/or pigments.

As used herein, "pigment" generally includes pigment colorants, magnetic particles, aluminas, silicas, and/or other ceramics, organo-metallics or other opaque particles, whether or not such particulates impart color. Thus, though the present description primarily exemplifies the use of pigment colorants, the term "pigment" can be used more generally to describe not only pigment colorants, but other pigments such as organometallics, ferrites, ceramics, etc. In one specific embodiment, however, the pigment is a pigment colorant.

As used herein, "dye" refers to compounds or molecules that impart color to a liquid vehicle or compound incorporating the dye. As such, dye includes molecules and compounds that absorb electromagnetic radiation or certain wavelengths thereof. For example, dyes include those that fluoresce as well as those that absorb certain wavelengths of visible light. Generally, dyes are water soluble.

As used herein, "binder" generally refers to a polymer or polymers used in inks such as liquid electrophotography inks or ink-jet inks.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

It has been recognized that it would be advantageous to develop methods, systems, and devices for measuring ionic particulates and/or determining the solid concentration in inks to improve printing and overall print performance. In accordance with this, the present disclosure is drawn to a device for measuring solid content of an ink, and associated methods and systems for determining solid contents of an ink. It is noted that when discussing the present devices or methods and systems associated with the devices, each of these discussions can be considered applicable to each of these embodiments, whether or not they are explicitly discussed in the context of that embodiment. Thus, for example, in discussing a deposition electrode in a device for measuring solid content of an ink, such a deposition electrode can also be used in a method or system for determining solid contents of an ink, and vice versa.

As such, with these definitions in mind, a device for determining solid content of an ink can comprise a chamber configured to hold an ink sample comprising ionic particulates in a liquid vehicle, a first opening in the chamber for filling the chamber with the ink sample, and a second distinct opening in the chamber for removal of the liquid vehicle. The device can also include a deposition electrode at least partially defining the chamber, a counter electrode, a power supply connected to the deposition electrode and counter electrode for creating an electric field inside the chamber, and a densitometer optically coupleable to the deposition electrode for measuring the optical density of ionic particulates. Additionally, the device can be operable to separate the ionic particulates from the liquid vehicle by deposition of the ionic particulates at the deposition electrode and/or the device can be operable to measure the optical density of the ionic particulates after migration to the deposition electrode.

Additionally, a method of determining solid content of an ink can comprise applying an electrical field to an ink sample using a deposition electrode and a counter electrode. The ink sample can comprise ionic particulates in a liquid vehicle and the electrical field can be sufficient to cause migration of ionic particulates in the ink sample to a deposition electrode from the liquid vehicle. Additional steps include measuring the content of the ionic particulates that have migrated and deposited on the deposition electrode and determining the solid contents of the ink from the content of the ionic particulates.

Further, a system for determining the solid contents of an ink can comprise a) an LEP ink sample comprising ionic particulates in a liquid vehicle and b) a device for determining the solid content of an ink. The device can comprise a chamber configured to hold an ink sample having ionic particulates in a liquid vehicle, a first opening in the chamber for filling the chamber with the ink sample, and a second distinct opening in the chamber for removal of the liquid vehicle. Additionally, the second opening can allow air to escape from the chamber when filling the chamber with ink. The device can also include a deposition electrode at least partially defining the chamber, a counter electrode, a power supply connected to the deposition electrode and the counter electrode for creating an electric field inside the chamber, and a densitometer optically coupleable to the deposition electrode for measuring the optical density of ionic particulates. Additionally, the solid content can be determined by converting the optical density measured using the densitometer to a solid content of the ink using a predetermined calibration curve for the ink.

Turning now to FIG. 1, a device 10 for separating ionic particulates from a liquid vehicle of an ink sample can comprise a chamber 12 generally defined by a portion of a top piece 16, at least a portion of a deposition electrode 18, a portion of a bottom piece 14, and a portion of a counter electrode 20. This configuration is merely exemplary of possible device structures and/or configurations. Additionally, the chamber can provide a constant volume for the ink sample when filling the chamber with an ink sample through a first opening 22 and allowing excess ink to flow out of a second opening 26 through an outlet 24 positioned such that the ink sample maintains contact with the deposition electrode. Additionally, air can escape the chamber through the second opening when filling the chamber with ink. While the discussion herein generally defines the device based on individual components and functionality, in one embodiment, the device can include the ink (not shown). In another aspect, the ink can be an LEP ink.

Additionally, a power supply 28 can be integrated into the device for providing an electric field in the chamber 12. In another embodiment, the power supply can be external to the device. Additionally, the device can have a DC-DC transformer 30 connected to the power supply. The DC-DC transformer can be present in order to modify the voltage from the power supply to produce an electric field sufficient to cause migration of ionic particulates in the ink sample and subsequent deposition on the deposition electrode 18. For example, in one embodiment, the power supply can be a battery. Additionally, the device can have a DC-DC transformer that increases the voltage from the battery sufficient to provide migration and deposition of the ionic particulates in the ink sample. In one specific embodiment, the battery can provide less than 10 volts and the DC-DC transformer can increase the battery voltage to at least 1000 volts. As such, for example, the DC-DC transformer can increase the voltage of the power supply to the deposition electrode by at least 10 fold. In one embodiment, the DC-DC transformer can increase the voltage of the power supply to the deposition electrode by at least 100 fold. Additionally, the increase can have incremental increases of 20 fold, 30 fold, 50 fold, or even 70 fold, or other incremental increases between these ranges.

While the dimensions of the device can vary, in one embodiment, the chamber can have a volume of about 0.3 cc to about 1 cc. Additionally, the first opening can have a cross-sectional area of about 1 mm$^2$ to about 5 mm$^2$. The second opening can have a cross-sectional area of about 5 mm$^2$ to about 20 mm$^2$. The outlet can have a cross-sectional area of about 0.5 mm$^2$ to about 1 mm$^2$. Additionally, the overall volume of the device can be from about 50 cc to about 200 cc. As shown in FIG. 1, the outlet can allow ink to flow out the second opening. As such, the channel between the second opening and the outlet can be sloped to further ease the excess ink flow; e.g., the present device takes advantage of gravity to remove the excess ink by having a downward slope from the outlet to the second opening.

Figure 2:
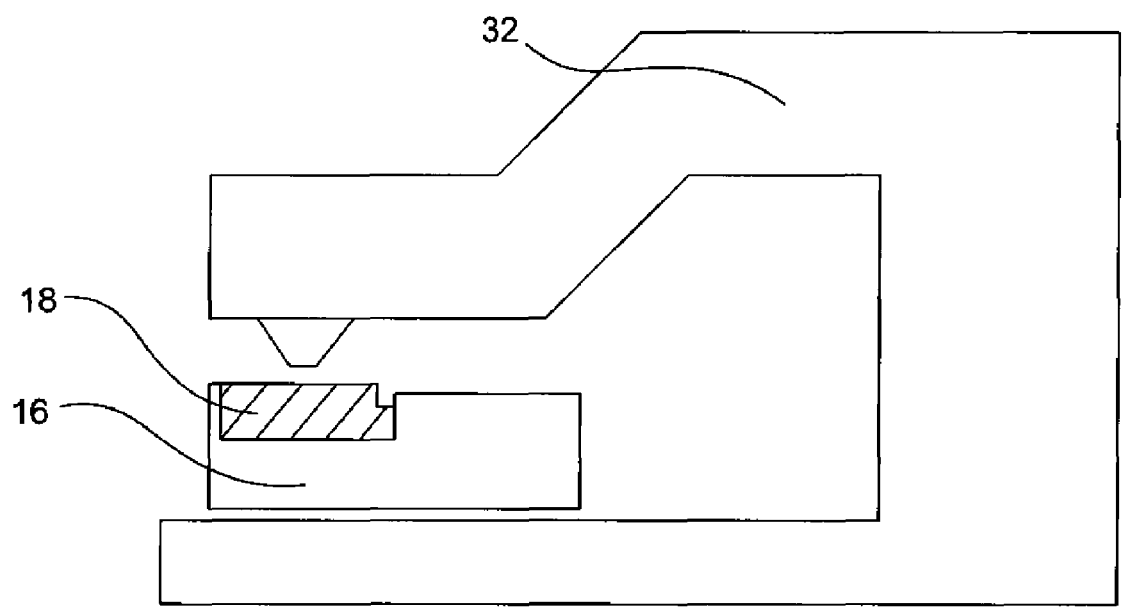
FIG. 2 is a front view of a top piece of a device with a deposition electrode on a densitometer in accordance with an embodiment of the present invention.

Turning now to FIG. 2, generally, the deposition electrode 18 can be removable from the device 10 and can be configured for use with a densitometer 32. For example, in one embodiment, the top piece 16 of the device having the deposition electrode can be removed and optically coupleable with a densitometer. However, the entire top piece need not necessarily be removed. Rather, in another embodiment, the deposition electrode can be individually removed from the top piece of the device and used with a densitometer. As such, when referring to removal of the electrode from the device, such removal can include removal of the top piece of the device or the individual removal of the electrode, unless otherwise indicated. Additionally, even though the electrode of the top piece of the device has been shown as the deposition electrode, the discussion herein is equally applicable to the counter electrode in the bottom piece of the device. In other words, the counter electrode can be used as a deposition electrode and configured with or optically coupleable with a densitometer as described herein. Further, although not required, after separation of the ionic particulates from the liquid vehicle, the excess liquid vehicle can be removed from the device before removal of the deposition electrode.

Generally, the densitometer can measure the optical density of the ionic particulates deposited on the deposition electrode. The optical density can then be converted to a solid content measurement by using a calibration curve predetermined for the ink measured. For example, if the ink is an LEP ink, after measuring the optical density of the ionic particulates from the LEP ink sample deposited at the electrode, the measurement can be converted to a solid content measurement or a colorant measurement by using a calibration curve for that specific LEP ink which accounts for any non-ionic solids or particulates that have not been deposited on the deposition electrode, for ionic solids or particulates that have a neutral charge, or for ionic solids or particulates that are repelled from the deposition electrode. The present discussion is not limited to LEP inks but can be used with any ink. As such, the optical density of the ionic particulates deposited at the deposition electrode can be corrected as described above for any ink.

Additionally, in one embodiment, the solid contents can refer to the colorant in the ink and determining the solid contents of the ink can be performed by converting the optical density to a colorant content of the ink using a predetermined calibration of the ink. In one embodiment, the measured optical density can be converted to % non-volatile solids (% NVS) of an ink. In one aspect, the measured solid content can have an accuracy within 5% of the actual solid content of the ink. In another aspect, the accuracy can be within 3%. In yet another aspect, the accuracy can be within 1%.

The deposition electrode or counter electrode can be positively charged or negatively charged and the targeted ionic particulates for deposition can be negatively charged or positively charged. The electrodes used herein can be of any metal alloy, conductive polymer, semiconductor, or material known to conduct electricity or sufficient to create an electric field sufficient to allow migration and deposition of ionic particulates in an ink. In one embodiment, the electrodes can be aluminum. In another embodiment, the electrodes can be stainless steel. Additionally, the surface of the electrodes can be treated such that the surface provides sufficient light scattering for use with a densitometer. As such, in one embodiment, the surface of the electrode can be treated or etched by mechanical means, e.g., with an abrasive. In another embodiment, the surface of the electrode can be treated or etched by chemical means, e.g., with an acid. Additionally, the electrodes can be individually selected from the materials described herein as well as further individually treated as described herein, and therefore, need not match as to material or treatment, although such a configuration may be present.

As discussed herein, the device can provide migration of the ionic particulates and deposition of the particulates on the deposition electrode. Such migration can be achieved by obtaining a certain electric field. Additionally, the ink sample can be diluted with a liquid that lowers the viscosity of the ink sample, provide better conductivity throughout the ink sample, or otherwise allows for easier migration of the ionic particulates to the electrode. The dilution of the ink sample can be in a ratio of liquid to ink sample of from about 2:1 to about 15:1. In another embodiment, the ratio can be from about 5:1 to about 10:1. The liquid used for dilution can be an aqueous or organic liquid. Additionally, the liquid is generally matched to the ink being used. In one embodiment, the liquid can be isoparaffinic oil. With these dilutions, in one embodiment, migration of the ionic particulates in the ink sample can be carried out at a voltage of less than about 500V, depending on the particulate concentration.

Additionally, the dilution need not be attributed to particle migration but may be performed to allow the appropriate signal detection when used with a densitometer. As such, in one embodiment, the ink can be diluted to a ratio that provides a detectable signal when separated and further measured with a densitometer. Further, the dilution can provide not only a detectable signal, but a signal that is sensitive to the amount of particulates deposited on the deposition electrode. Such sensitivity can allow measurable differences in solid contents between inks having differing amounts of solid contents using a densitometer and converting the optical density measurement to a solid content measurement using a calibration curve as discussed herein. As such, in one embodiment, the sensitivity can distinguish between differing amounts of solid contents deposited on the deposition electrode and/or the solid contents as determined using a calibration curve for the ink.

When referring to electrode, such a reference can refer to either the deposition electrode or counter electrode unless the context dictates otherwise. Additionally, while the present discussion generally refers to a deposition electrode and a counter electrode, it is understood that the counter electrode can also cause migration of ionic particulates and subsequent deposition of such particulates. However, such particulates deposited on the counter electrode would contain ionic material oppositely charged than that of the deposition electrode. Additionally, it is noted that the counter electrode could have non-ionic materials deposited thereon due to gravitational effects as the counter electrode is orientated on the bottom portion of the device. Even so, the counter electrode may also be used with the methods and systems described herein.

As discussed herein, in one embodiment, the ink can be an LEP ink. Such an LEP ink can further comprise charge directors, electric stability additives, binders, etc., as is known in the art.

The colorants dispersed in the liquid vehicle can be any colorant compatible with the liquid vehicle and useful for printing. The colorants can include, but are not limited to, cyan colorants, magenta colorants, yellow colorants, violet colorants, orange colorants, green colorants, black colorants, and combinations thereof. Colorants used in conjunction with inks are known in the art. In one embodiment, the colorant can be those used with ink-jet inks. In another embodiment, the colorant can be those used with LEP inks. The pigment can be from about 0% to 80% by total weight of the ink.

Additionally, other additive may be present in the ink. One or more non-ionic, cationic, and/or anionic surfactant can be present, ranging from 0.01 wt % to 5 wt %. The balance of the formulation can be other liquid vehicle components known in the art, such as biocides, organic solvents, viscosity modifiers, materials for pH adjustment, sequestering agents, preservatives, compatibility additives, emulsifiers, and the like.

EXAMPLES

The following examples illustrate embodiments of the disclosure that are presently known. Thus, these examples should not be considered as limitations of the invention, but are merely in place to teach how to make compositions of the present disclosure. As such, a representative number of compositions and their method of manufacture are disclosed herein.

Example 1

Separation of Ionic Particulates of Cyan Inks having Varying Solid Contents

A sample of cyan inks having varying solid contents were diluted about 10:1 with isoparaffinic oil. The diluted ink samples were introduced into the chamber of a device of the present invention having batteries supplying 4 volts with a DC-DC transformer increasing the voltage to aluminum electrodes to 1300 volts. The chamber was about 600 microns wide with a volume of about 0.3 cc. The voltage was applied for about 3 seconds after which excess liquid vehicle was removed.

Example 2

Measurement of Optical Density

The top piece of the device containing the deposition electrode was removed and placed under an X-rite densitometer Series 500 for optical density measurement for the Cyan Inks of Example 1. The optical density was measured on 4 channels (V,C,M,Y) for each of the cyan inks with the results present below in Table 1:

TABLE 1

| Non-volatile Solids in the Cyan Ink | Channel of Xrite Densitometer | | | |
|---|---|---|---|---|
| (% NVS) | V | C | M | Y |
| 0.151466 | 0.76 | 0.93 | 0.62 | 0.52 |
| 0.181679 | 0.81 | 1.02 | 0.65 | 0.51 |
| 0.209841 | 0.83 | 1.08 | 0.65 | 0.5 |
| 0.272662 | 0.91 | 1.25 | 0.68 | 0.5 |
| 0.299039 | 0.94 | 1.33 | 0.7 | 0.52 |
| 0.642669 | 1.16 | 2.06 | 0.81 | 0.49 |

The results show that the optical density measurement corresponded to the % NVS of diluted ink. Further, the results show that specific channels can be selected for improved sensitivity.

Example 3

Creating Calibration Curve

A yellow ink having 2% NVS in a liquid vehicle of (HP Indigo imaging oil) isoparaffinnic oil was prepared. The ink was further diluted to create a series of calibrated inks having % NVS as presented in Table 2 below. The results were calibrated using an exponential fit of equation 1.

TABLE 2

| Yellow Ink | Channel of X-rite Densitometer | | | | Calibration Exponential |
|---|---|---|---|---|---|
| % NVS | V | C | M | Y | fit to Y |
| 0 | 0.49875 | 0.505 | 0.4925 | 0.48875 | 0.489 |
| 0.46 | 0.4425 | 0.4225 | 0.4725 | 1.4675 | 1.477084 |
| 0.21 | 0.4725 | 0.4675 | 0.48 | 1.08 | 1.077794 |
| 0.34 | 0.4525 | 0.4375 | 0.4725 | 1.335 | 1.326753 |
| 0.14 | 0.485 | 0.4825 | 0.4825 | 0.89 | 0.910034 |
| 0.27 | 0.465 | 0.455 | 0.475 | 1.2175 | 1.203935 |

$$OD = o + A(1 - e^{-c}/C_0) \quad \text{Equation 1}$$

The results of Table 2 show that an exponential fit using equation 1 provide accurate predicted measurements. For Equation 1, o, A, and $C_0$ are constants, OD is optical density, and c is the concentration of NVS. Specifically, the exponential OD measurements derived from the concentration shows high predictable with the observed OD measurements.

Example 4

Determining % NVS from OD Measurements for an Ink Set

An inkset having a various colorants in a liquid vehicle was prepared in accordance with Example 3. The inkset comprised a yellow ink, a magenta ink, a cyan ink, and a black ink. The ink was diluted to create a series of calibrated inks having % NVS as presented in Table 3 below. The diluted ink samples were introduced into the chamber of a device of the present invention having batteries supplying 4 volts with a DC-DC transformer increasing the voltage to aluminum electrodes to 1300 volts. The deposition electrode was removed and measured by X-rite densitometer Series 500 to provide optical density measurements which were then converted to % NVS based on the calibration data from Equation 1 from Example 3. Table 3 provides the results.

TABLE 3

| Ink | Actual % NVS | Predicted % NVS | Difference |
|---|---|---|---|
| Yellow | 2.33 | 2.33 | 0.00 |
| Magenta | 2.12 | 2.21 | 0.09 |
| Cyan | 2.12 | 2.19 | 0.07 |
| Black | 2.20 | 2.29 | 0.09 |

The results of Table 3 show that the predetermined calibration curve developed from Example 3 provides an accurate measurement of % NVS present in the ink sample. Based on these results, a method of determining solid contents of an ink can be performed by separating the ionic particulates from the liquid vehicle of an ink, measuring the deposited ionic particulates using a densitometer, and then converting the optical density measurement to a solid content measurement using a predetermined calibration curve for the ink.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

What is claimed is:

1. A device for determining solid content of an ink, comprising:
    a chamber configured to hold an ink sample comprising ionic particulates in a liquid vehicle;
    a first opening in the chamber for filling the chamber with the ink sample;
    a second distinct opening in the chamber for removal of the liquid vehicle;
    a deposition electrode at least partially defining the chamber;
    a counter electrode;
    a power supply connected to the deposition electrode and the counter electrode for creating an electric field inside the chamber; and
    a densitometer optically coupleable to the deposition electrode for measuring the optical density of ionic particulates;
    wherein the device is operable to separate the ionic particulates from the liquid vehicle by deposition of the ionic particulates at the deposition electrode, and wherein the device is operable to measure the optical density of the ionic particulates after migration to the deposition electrode.

2. The device of claim 1, wherein the device contains the ink.

3. The device of claim 2, wherein the ink is an LEP ink.

4. The device of claim 1, wherein the densitometer is configured to measure the optical density of the ionic particulates located at the deposition electrode after at least a portion of the liquid vehicle is removed.

5. The device of claim 1, wherein the electrode is mechanically etched or chemically etched.

6. The device of claim 1, wherein the power supply is a battery.

7. The device of claim 1, further comprising a DC-DC transformer connected to the power supply.

8. The device of claim 7, wherein the DC-DC transformer increases the voltage of the power supply to the deposition electrode by at least 10 fold.

9. The device of claim 1, wherein the chamber further comprises an outlet positioned to allow excess ink to flow out of the second opening, thereby providing a constant maximum volume of ink allowable the chamber.

10. The device of claim 1, wherein the counter electrode at least partially defines the chamber.

11. The device of claim 10, wherein at least one of the deposition electrode and the counter electrode is removable from the device.

12. A method of determining solid content of an ink, comprising:
   applying an electrical field to an ink sample using a deposition electrode and a counter electrode, said ink sample comprising ionic particulates in a liquid vehicle and said electrical field sufficient to cause migration of ionic particulates in the ink sample to a deposition electrode from the liquid vehicle;
   measuring the content of the ionic particulates that have migrated and deposited on the deposition electrode by measuring the optical density of the ionic particulates using a densitometer; and
   determining the solid contents of the ink from the content of the ionic particulates.

13. The method of claim 12, wherein the step of determining the solid contents of the ink is corrected for non-ionic particulates.

14. The method of claim 12, wherein the solid content of the ink is colorant, and the step of determining the solid contents of the ink is performed by converting the optical density to a colorant content of the ink using a predetermined calibration curve for the ink.

15. The method of claim 12, further comprising diluting the ink sample with a liquid to provide a detectable signal when measured with a densitometer.

16. The method of claim 12, wherein the ink is an LEP ink.

17. The method of claim 12, further comprising using a device comprising:
   a chamber configured to hold an ink sample having ionic particulates in a liquid vehicle;
   a first opening in the chamber for filling the chamber with the ink sample;
   a second distinct opening in the chamber for removal of the liquid vehicle;
   a deposition electrode at least partially defining the chamber;
   a counter electrode;
   a power supply connected to the deposition electrode and the counter electrode for creating an electric field inside the chamber; and
   a densitometer optically coupleable to the deposition electrode for measuring the optical density of ionic particulates.

18. The method of claim 17, wherein measuring the content of ionic particulates is performed by measuring the optical density of the ionic particulates using the densitometer, wherein the solid contents of the ink are colorants, and wherein determining the solid contents of the ink is performed by converting the optical density to a colorant content of the ink using a predetermined calibration curve for the ink.

19. A system for determining the solid contents of an ink, comprising
   a) an LEP ink sample comprising ionic particulates in a liquid vehicle; and
   b) a device, comprising:
      i) a chamber configured to hold an ink sample having ionic particulates in a liquid vehicle;
      ii) a first opening in the chamber for filling the chamber with the ink sample;
      iii) a second distinct opening in the chamber for removal of the liquid vehicle;
      iv) a deposition electrode at least partially defining the chamber;
      v) a counter electrode;
      vi) a power supply connected to the deposition electrode and the counter electrode for creating an electric field inside the chamber; and
      vii) a densitometer optically coupleable to the deposition electrode for measuring the optical density of ionic particulates,
   wherein the solid content is determined by converting the optical density measured using the densitometer to a solid content of the ink using a predetermined calibration curve for the ink.

* * * * *